United States Patent
Derbre et al.

(10) Patent No.: US 9,107,849 B2
(45) Date of Patent: Aug. 18, 2015

(54) **ANTI-GLYCATION AGENT COMPRISING A *GARCINIA KOLA* EXTRACT OR FRACTION**

(71) Applicants: UNIVERSITE D'ANGERS, Angers (FR); LABORATOIRE SHIGETA, Paris (FR)

(72) Inventors: Severine Derbre, Angers (FR); Sylvie Morel, Fraize (FR); Pascale Richomme, Angers (FR); Alexis Kaatio Toure, Issy les Moulineaux (FR)

(73) Assignees: UNIVERSITE D'ANGERS, Angers (FR); LABORATOIRE SHIGETA, Paris (FR)

( * ) Notice: Subject to any disclaimer, the term of this patent is extended or adjusted under 35 U.S.C. 154(b) by 0 days.

(21) Appl. No.: 14/083,768

(22) Filed: Nov. 19, 2013

(65) Prior Publication Data

US 2014/0142171 A1    May 22, 2014

(30) Foreign Application Priority Data

Nov. 21, 2012    (FR) ...................................... 12 61090

(51) Int. Cl.
| | | |
|---|---|---|
| *A61K 36/00* | (2006.01) | |
| *A61K 8/49* | (2006.01) | |
| *A61Q 19/08* | (2006.01) | |
| *A61K 8/97* | (2006.01) | |
| *A61K 31/353* | (2006.01) | |
| *A61K 36/38* | (2006.01) | |

(52) U.S. Cl.
CPC . *A61K 8/498* (2013.01); *A61K 8/97* (2013.01); *A61K 31/353* (2013.01); *A61K 36/38* (2013.01); *A61Q 19/08* (2013.01); *A61K 2236/00* (2013.01)

(58) Field of Classification Search
None
See application file for complete search history.

(56) References Cited

U.S. PATENT DOCUMENTS

2005/0245600 A1* 11/2005 Urade et al. .................. 514/456

FOREIGN PATENT DOCUMENTS

| JP | 2001226249 | | 8/2001 |
|---|---|---|---|
| JP | 2001226249 A | * | 8/2001 |

OTHER PUBLICATIONS

Okunji et al, Preparative isolation and identification of tyrosinase inhibitors from the seeds of Garcinia kola by high-speed countercurrent chromatography. Journal of Chromatography A (2007), 1151(1-2), 45-50.*

Reddy et al. "Inhibitors of the Maillard reaction and Age breakers as therapeutics for multiple diseases", Drug Discovery Today, vol. 11, No. 13/14, Jul. 2006, pp. 646-654.
Derbre et al. "Automating a 96-well microtiter plate assay for identification of AGEs inhibitors or inducers: application to the screening of a small natural compounds library", Analytical and Bioanalytical Chemistry, vol. 398, No. 4, Sep. 2010, pp. 1747-1758.
Pageon et al. "Reconstructed skin modified by glycation of the dermal equivalent as a model for skin aging and its potential use to evaluate anti-glycation molecules", Experimental Gerontology J, vol. 43, No. 6, Jun. 2008, pp. 584-588.
Urios P. et al. "Flavonoids inhibit the formation of the cross-linking AGE pentosidine in collagen incubated with glucose, according to their structure", European Journal of Nutrition, vol. 46, No. 3, Apr. 2007, pp. 139-146.
Cervantes-Laurean D. et al. "Inhibition of advanced glycation end product formation on collagen by rutin and its metabolites", Journal of Nutritional Biochemistry, vol. 17, N°8, Jan. 2006, pp. 531-540.
Iwu M. et al. "Evaluation of the antihepatotoxic activity of the biflavonoids of *Garcinia kola* seed", Journal of Ethnopharmacology, vol. 21, No. 2, Nov. 1987, pp. 127-138.
Farombi E. O. et al. "Antioxidative and chemopreventive properties of *Vernonia amygdalina* and *Garcinia* biflavonoid", International Journal of Environmental Research and Public Health, vol. 8, No. 6, Jun. 2011, pp. 2533-2555.
Adefule-Ositelu A. O. et al. "Efficacy of *Garcinia kola* 0.5% aqueous eye drops in patients with primary open-angle glaucoma or ocular hypertension", Middle East African Journal of Ophthalmology, vol. 17, No. 1, Jan.-Mar. 2010, pp. 88-93.
Adegbehingbe O. O. et al. "Clinical effects of *Garcinia kola* in knee osteoarthritis", Journal of Orthopaedic Surgery and Research, vol. 3, Jul. 2008, pp. 34.
Zhang J.-H. et al. "A simple statistical parameter for use in evaluation and validation of high throughput screening assays", Journal of Biomolecular Screening, vol. 4, No. 2, Apr. 1999, pp. 67-73.
Grandhee S. K. et al. "Mechanism of formation of the Maillard protein cross-link pentosidine", The Journal of Biological Chemistry, vol. 266, No. 18, Jun. 1991, pp. 11649-11653.
Peng X, et al. "Naturally occurring inhibitors against the formation of advanced glycation end-products", Food & function, vol. 2, No. 6, May 2011, pp. 289-301.
Okunji et al.,"Preparative isolation and identification of tyrosinase inhibitors from the seeds of *Garcinia kola* by high-speed countercurrent chromatography", Journal of Chromatography A, vol. 1151, N°1-2, Mar. 2007, pp. 45-50.
European Search report, dated Feb. 28, 2014, from the patent application EP 13193929.
Iwu M. M. "Antihepatoxic constituents of *Garcinia kola* seeds", Experientia, vol. 41, No. 5, 1985, pp. 699-700.
Jangu M. J. et al. "Anti-AGEs activity screening of molecules isolated from Tanzanian clusiaceous species", Planta Medica, vol. 78, No. 11, Jul. 2012.

* cited by examiner

*Primary Examiner* — Qiuwen Mi
(74) *Attorney, Agent, or Firm* — Young & Thompson

(57) ABSTRACT

An anti-glycation agent includes a *Garcinia kola* extract or fraction. The compositions including the extract or the fraction are used to inhibit the glycation of proteins, in particular the glycation of skin proteins involved in cutaneous aging. A method for determining the activity of compounds for inhibiting the glycation of cutaneous proteins, in particular for inhibiting the glycation of collagen is also described.

6 Claims, 4 Drawing Sheets

ANTI-GLYCATION AGENT COMPRISING A *GARCINIA KOLA* EXTRACT OR FRACTION

FIELD OF THE INVENTION

This invention relates to an anti-glycation agent comprising a *Garcinia kola* extract or fraction. The invention also relates to the use of the anti-glycation agent according to the invention for inhibiting the glycation of proteins, in particular the glycation of proteins of the skin involved in cutaneous aging, in particular collagen. This invention also relates to a method for determining the activity of compounds for inhibiting the glycation of cutaneous proteins, in particular for inhibiting the glycation of collagen.

PRIOR ART

Non-enzymatic glycation reactions, also called browning reactions, were first described in 1912 by Maillard (*C. R. Acad. Sci.* 1912, 154, 66-67). More specifically, it is a cascade of reactions involving reducing sugars and proteins and leading to a multitude of glycation end products, more commonly called "Advanced Glycation End-products" (AGEs), as shown in FIG. 1.

The glycation observed in the Maillard reaction is a non-enzymatic process involving a sugar, such as, for example, glucose, fructose or ribose, which reacts with the primary amine of an amino acid residue, such as, for example, lysine or arginine, particularly an amino acid residue of a protein, to form a Schiff base. This, after a molecular rearrangement called an Amadori rearrangement, can lead, by a series of reactions, in particular of oxidation and cyclization, to the formation of AGEs. The latter are, for example, pyrraline, pentosidine, crossline, Nε(2-carboxyethyl)-lysine (CEL), glyoxal-lysine dimer (GOLD), methylglyoxal-lysine dimer (MOLD), 3DG-ARG imidazolone or versperlysines A, B, C.

From a biological perspective, the phenomenon of protein glycation is accentuated with the aging of the tissues. It is thus characterized by the appearance of AGEs of which the content increases regularly over time. The cross-linking of proteins, induced by this process, leads to the alteration of the structure and therefore the function thereof. Moreover, when AGEs interact with their specific receptors or RAGEs, this leads to an increase in the production of ROS (Reactive Oxygen Species), which leads in particular to the activation of transcription factors such as NF-κB. In many cells, the transcription of genes regulated by NF-κB induces an inflammatory process and pathological changes (Alexiou et al. *Curr. Med. Chem.*, 2010, 17, 2232-2252; Brownlee *Nature*, 2001, 414, 813-820; Ferchichi et al. *Phytochemistry*, 2012, 78, 98-106; Srikanth et al. *Neurobiol. Aging*, 2011, 32, 763-777).

The formation of AGEs increases progressively with aging and is accelerated in different pathologies (V. P. Reddy et al. *Drug Discov. Today* 2006, 11, 646). In particular, AGEs cause damage that may be the origin of general skin aging phenomena such as loss of elasticity, drying, thinning, appearance of spots, stiffening, and appearance of lines and wrinkles. In the case of skin, it is primarily the glycation of collagen fibers that is responsible for cutaneous aging.

Molecules capable of inhibiting the formation of AGEs and/or destroying them ("Advanced Glycation End products inhibitors and/or Breakers"—AGEIBs) are therefore good candidates as active cosmetic agents, in particular for fighting aging.

There are three mechanisms whereby these molecules exert their anti-AGE activity (Peng et al. *Food Funct.* 2011, 2, 289, FIG. 1):

- by inhibiting the oxidation of reducing sugars such as glucose or ribose into dicarbonyl products (methylglyoxal, glyoxal, 1-deoxyglucosone, 3-deoxyglucosone) or by inhibiting the oxidation of Amadori products into post-Amadori dicarbonyl products;
- by trapping the dicarbonyl products, whether they are glyoxal, methylglyoxal, 1-deoxyglucosone, 3-deoxyglucosone or post-Amadori products (e.g. aminoguanidine, catechins, procyanidins);
- by breaking the post-Amadori products. These products are AGEs breakers.

Anti-AGEs molecules may also be antioxidants, i.e. molecules capable of trapping reactive oxygen species (ROS) or capable of complexing the metal cations involved in the Fenton reaction (e.g. polyphenols). However, molecules or extracts without or with a weak antioxidant activity may be anti-AGEs. Also, there is no established correlation between the magnitude of the antioxidant activity and the magnitude of the anti-AGEs activity.

A certain number of active agents, natural or synthetic, are known for their anti-glycation effect, such as aminoguanidine, quercetin, garcinol, benfotiamine, pyridoxamine, ergothioneine, resveratrol, curcumin, carnosine, rutin or guanidine. Plant extracts may also be used, such as cornflower, green tea or thyme extracts, or extracts of plants of the Hypericaceae or Ericaceae families.

However, the AGEIBs cited above do not have a significant anti-glycation activity for the skin proteins involved in cutaneous aging. Moreover, in the case of plant extracts, problems of supply, production costs and preservation of biodiversity may limit their availability.

There is thus a need to find new AGEIBs that are effective against cutaneous aging, non-toxic, accessible and the exploitation of which is environmentally friendly.

In view of this need, the Applicant was faced with the need to find a means for selecting and evaluating the anti-AGEs activity of plant molecules and extracts in order to identify anti-AGEs molecules effective in fighting cutaneous aging.

The anti-AGEs activity of compounds can be determined by immunochemical tests using monoclonal antibodies. However, these tests have the disadvantage of being costly and difficult to adapt to high-speed screening.

Enzymatic tests are also used to determine anti-AGEs activities. This type of test consists of evaluating the inactivation of the RNase under conditions promoting the formation of AGEs. However, this test is not specific to skin proteins and is not representative of cutaneous aging phenomena associated with the glycation of skin proteins.

The inhibition of the formation of AGEs can also be evaluated on reconstructed skin or on skin explants. However, this method is not compatible with rapid or high-speed screening (Pageon et al. *Exp. Gerontol.* 2008, 43, 584-588).

Methods based on the specific fluorescence detection of certain AGEs, in particular vesperlysines and sometimes pentosidine, are widely used to evaluate anti-AGEs activity. In these tests, bovine albumin is used as a model protein whereas various sugars, glycation agents (glucose, fructose, ribose), are used. These tests consist of detecting the formation of AGEs by fluorescence in a solution containing albumin, a sugar and the AGEIB to be tested, at a pH close to that of the skin. These tests are often performed over a period ranging from 7 to 30 days. Recently, a test performed in 24 hours using albumin and ribose was developed (Derbré et al. *Anal. Bioanal. Chem.* 2010, 398, 1747-1758). However, albumin is a protein that is not present in the skin. Consequently, the compounds identified by this type of test have a demonstrated albumin glycation inhibiting activity, but this does not anticipate their activity on proteins present in the skin.

It would thus be desirable to have a new method making it possible to select and evaluate the anti-AGEs activity of molecules and/or plant extracts in order to fight the glycation of skin proteins and consequently fight cutaneous aging. This new method must also be quick, automatable and compatible with high-speed screening.

The solution envisaged by the Applicant is to develop a new fluorimetric method using, as the test protein, a characteristic skin protein known to be involved in aging, such as collagen. Collagen is particularly valuable as a test protein because it contains numerous lysine residues, making it very sensitive to glycation.

To the Applicant's knowledge, only two examples of the use of collagen for evaluating anti-glycation activity have been reported:

the use of non-soluble type-I collagen and glucose in a test for determining the activity of AGEIBs with fluorescence detection of the pentosidine formed (Urios et al. *Eur. J. Nutr.* 2007, 46, 139-146). The formation of pentosidine is measured by CLHP after 28 days of incubation. The AGEIBs identified by this test on collagen are intended to prevent the development of vascular complications in patients with diabetes;

under similar conditions (suspended type-I collagen and glucose), the fluorescence of the AGEs formed, and in particular pentosidine, was evaluated after 16 days of incubation (Cervantes-Laurean et al. *J. Nutr. Biochem.* 2006, 17, 531-540). As in the study above, the AGEIBs identified may play a role in patients with diabetes.

These tests on collagen are therefore long (from 1 to 4 weeks). Moreover, the insolubility of collagen in the aqueous buffers used in these tests does not enable automated pipetting operations. These conditions are therefore unsuitable for the rapid or high-speed screening sought by pharmaceutical and cosmetic industries.

The Applicant therefore developed a new rapid and automatable method making it possible to determine the glycation-inhibiting activity on cutaneous proteins, in particular collagen, of compounds and/or plant extracts. The method of the invention makes it possible to obtain a result within 24 hours and uses collagen solubilized in an acid medium, prior to incubation. The method of the invention makes it possible to compare the activities of pure molecules and molecules in mixtures, comprising those obtained from plant extracts.

The implementation of the method of the invention made it possible to evaluate plant extracts for their anti-glycation activity. In particular, the Applicant demonstrated that *Garcinia kola* extracts have a very strong glycation-inhibiting activity on collagen. Without willing to be linked by any theory, it appears that the biflavonoids present in the *Garcinia kola* extract of the invention play a major role in the collagen anti-glycation activity identified.

*Garcinia kola* is a plant cultivated in a number of African countries, in particular in Nigeria, and the fruits and seeds of which are nutritionally valuable. Locally, *Garcinia kola* is used primarily as a medicinal plant. *Garcinia kola* extracts are used in particular in traditional medicine to treat bronchitis, laryngitis, oral infections, colic, dysentery and headaches. Various studies have made it possible to demonstrate the efficacy of this plant for treating the conditions cited but also ocular and liver diseases, bacterial and viral infections or osteoarthritis (Iwu et al. *J. Ethnopharmacol.* 1987, 21, 127-138, Farombi et al. *Int. J. Environ. Res. Public Health* 2011, 8, 2533-2555, Adefule-Ositelu et al. *Middle East Afr. J. Ophthalmol.* 2010, 17, 88-83, Adegbehingbe et al. *J. Orthop. Surg. Res.* 2008, 3, 34).

The Applicant thus found that, surprisingly, *Garcinia kola* extracts have an anti-glycation activity. To the Applicant's knowledge, no composition comprising *Garcinia kola* extracts used as anti-glycation agents, in particular for fighting skin aging, has yet been reported.

DETAILED DESCRIPTION

*Garcinia kola* Extract

According to a first aspect, the invention relates to an anti-glycation agent comprising a *Garcinia kola* extract. In one embodiment, the *Garcinia kola* extract is obtained from *Garcinia kola* seeds, fruits, epicarp, leaves, bark, wood or roots, and preferably from *Garcinia kola* seeds. Advantageously, the *Garcinia kola* parts extracted are first dried. Preferably, the extract is obtained from dried *Garcinia kola* seeds. In a preferred embodiment, the *Garcinia kola* seeds are dried then ground prior to extraction.

In one embodiment, the anti-glycation agent according to the invention, comprising a *Garcinia kola* extract, comprises at least one biflavonoid, preferably selected from the group comprising GB1, GB1a, GB2, kolaflavanone. According to one embodiment, the *Garcinia kola* extract is rich in biflavonoids, preferably rich in at least one biflavonoid selected from GB 1, GB 1a, GB2 and kolaflavanone. According to one embodiment, a biflavonoid-rich extract comprises a concentration of more than 5% biflavonoids expressed in GB2 equivalents, assayed by HPLC-UV at 290 nm, preferably more than 40% biflavonoids expressed in GB2.

In one embodiment, the *Garcinia kola* extract also comprises garcinoic acid.

In a first embodiment, the extract is liquid. In a second embodiment, the extract is a dry extract.

Extraction Process

According to a second aspect, the present invention also relates to a process for extracting active agents from plants, preferably from *Garcinia kola* seeds, comprising placing the plant material to be extracted, preferably dried and/or preferably ground, in contact with a solvent, then extraction at high temperature and pressure.

According to a first preferred embodiment, the extract is obtained by extraction under pressure, preferably using the Büchi Speed Extractor. This extraction method allows to reduce the consumption of solvent and to increase the extraction speed. In this method, the solvent is preferably introduced at high pressure and temperature into the extraction vessel containing the matrix to be extracted. The high temperature increases the solubility of the substances of interest in the extraction solvent and accelerates their matrix desorption kinetics. In this embodiment, the solvent used for the extraction is water, an alcohol, a hydrocarbon, a halogenated hydrocarbon, acetone, ethyl acetate or a mixture of these solvents. In a preferred embodiment, the alcohol is methanol or ethanol, preferably ethanol. In a preferred embodiment, the extraction solvent is a mixture of water-alcohol, preferably a mixture of water-ethanol, in which the two solvents are preferably in 1:1 proportions. In another embodiment, the solvent is ethyl acetate. Preferably, the extraction is performed at a temperature ranging from 40 to 200° C., preferably 50 to 150° C., more preferably 80 to 120° C., even more preferably around 100° C. In this embodiment, the extraction is performed at a pressure ranging from 50 to 150 bars, preferably 80 to 120 bars, more preferably around 100 bars. Preferably, 2 to 5 extraction cycles are performed, preferably 3 extraction cycles lasting between 2 and 20 m, preferably 2 min to 10 min.

In one embodiment, a plurality of successive extractions are performed. In one embodiment, a plurality of successive extractions are performed with different solvents.

In a second preferred embodiment, the extraction is a supercritical extraction, preferably in the presence of supercritical $CO_2$ as the solvent.

In a third preferred embodiment, the extraction is a subcritical extraction, preferably in the presence of subcritical water as the solvent.

In one embodiment, at the end of the extraction, the solvent containing the extract is partially or completely evaporated so as to provide the liquid or dry biflavonoid-rich extract of the invention. The extraction yield is greater than 3% m/m, and preferably the extraction yield is between 10 and 15% m/m.

The extraction device can be a conventional extraction device known to a person skilled in the art such as, for example, a maceration device, a Soxhlet-type apparatus, a supercritical or subcritical extractor, or an accelerated solvent extraction apparatus.

*Garcinia kola* Extract Fraction and Fractionation Process

According to a third aspect, this invention also relates to an anti-glycation agent comprising a *Garcinia kola* fraction rich in at least one biflavonoid selected from the group comprising GB 1, GB 1a, GB2 and kolaflavanone, characterized in that it comprises a total biflavonoid concentration of more than 5%, preferably more than 20%, preferably more than 40% biflavonoids expressed in GB2 equivalents, assayed by HPLC-UV at 290 nm.

According to a first embodiment, the fraction is obtained by implementing a *Garcinia kola* extract fractionation process described above or obtained by the extraction process of the invention, said fractionation being performed by normal-phase liquid chromatography on a solid support, by reverse-phase liquid chromatography on a solid support, by atmospheric-pressure liquid chromatography, by medium-pressure liquid chromatography, by high-performance liquid chromatography, by flash chromatography, by countercurrent chromatography, or by a combination of these methods.

According to a second embodiment, the fraction is obtained by filtration on polyamide of a solution comprising the extract described above. This type of filtration allows to remove all or some of the tannins present in the extract and thus enrich the biflavonoid fraction. In one embodiment, the solution used for the filtration is alcoholic, preferably an ethanol solution.

According to a third embodiment, the fraction of the invention is obtained by precipitation.

In one embodiment, the fraction of the invention is a dry fraction.

In a particular embodiment, different fractions of the *Garcinia kola* extract are obtained by fractionation by chromatography, preferably by silica gel chromatography with a polar eluent, preferably a mixture of dichloromethane and methanol. In this embodiment, the fractions are rich in biflavonoids such as, for example GB1, GB 1a, GB2 or kolaflavanone, garcinoic acid, polyols, flavonoids, sugars or tannins.

Composition Comprising an Anti-Glycation Agent According to the Invention

The invention also relates to a composition comprising an anti-glycation agent comprising a *Garcinia kola* extract of the invention or a *Garcinia kola* fraction of the invention. In one embodiment, the composition of the invention comprises 0.1 to 2% of *Garcinia kola* extract of the invention in weight relative to the total weight of the composition. In another embodiment, the composition of the invention comprises 0.1 to 2% of the fraction of the invention in weight relative to the total weight of the composition.

In one embodiment, the composition of the invention is a cosmetic composition, which comprises a *Garcinia kola* extract or a *Garcinia kola* fraction, in association with a cosmetically acceptable carrier, which may preferably be a cosmetic base or a cosmetically acceptable oil. According to one embodiment, the composition of the invention comprises 0.1 to 2% *Garcinia kola* extract of the invention in weight relative to the total weight of the composition and a cosmetically acceptable carrier. In one embodiment, the cosmetic base comprises at least one compound selected from the group comprising at least one consistency factor, at least one emollient, at least one surfactant and at least one preservative or a mixture of these compounds.

In one embodiment, the composition of the invention also comprises at least one compound selected from the group comprising consistency factors such as a *butyrospermum parkii* extract (shea butter), glyceryl dibehenate, cetearyl alcohol, illipe butter, glyceryl undecylenate or tribehenin; emollients such as apricot kernel oil, *Rosa Rubiginosa* seed oil, octyldodecyl myristate, coco caprylate, capric/caprylic triglyceride, or propanediol dicaprylate; emulsifiers such as glyceryl stearate; surfactants such as coco glucoside; thickeners such as corn starch; stabilizers; moistening agents such as glycerin or diglycerin; gelling agents such as xanthan gum; fragrances; preservatives such as gluconolactone, sodium benzoate, benzyl alcohol or dehydroacetic acid; dyes; pH adjusters such as sodium hydroxide; or a mixture of these compounds.

In one embodiment, the composition also comprises a compound selected from the group comprising antioxidants such as tocopherol; UV filters; skin relaxants; anti-glycation agents; lipolytic agents; anti-irritants; hydrating agents such as trehalose, sodium hyaluronate, damask rose water; rye seed extract, *Chondrus Crispus* extract or *Aloe Barbadensis* leaf juice powder; antibacterial agents; antimicrobial agents; antifungal agents; anti-allergenic agents; antibiotics; anti-acne agents; nutrients such as vitamins; whitening agents; chelating agents such as phytic acid; feel agents such as polylactic acid or lauroyl lysine; or a mixture of these compounds.

In one embodiment, the composition of the inventions does not include tocol or one of its salts of derivatives. In another embodiment, the composition of the invention does not include tocotrienols or one of its salts of derivatives. In another embodiment, the composition of the invention does not include tocopherol, or one of its salts of derivatives.

According to one embodiment, the composition of the invention also comprises compounds commonly used in cosmetic compositions and known to a person skilled in the art.

In one embodiment, the composition of the invention is in the form of a solution, an emulsion, a suspension or a paste. In one particular embodiment, the composition of the invention comprises a cosmetic base and water and is in the form of an oil-in-water or a water-in-oil emulsion.

In one embodiment, the composition is in a topically administrable form. In this embodiment, the composition of the invention may be in any form conventionally used for topical administration such as, for example, a cream, a milk, a serum, a mask, an aqueous gel, a pomade, a lotion, an emulsion, a foam, a suspension or a paste.

According to one embodiment, the composition of the invention is stable for a period of at least one year under standard storage conditions.

Use of the *Garcinia kola* Extract, the Fraction and/or the Composition of the Invention This invention also relates to the use of the de *Garcinia kola* extract, the fraction and/or the composition of the invention for inhibiting glycation of proteins, preferably skin proteins, more preferably collagen.

The *Garcinia kola* extract or fraction described above is used as an anti-glycation agent for preventing and/or fighting cutaneous aging.

In one embodiment, the anti-glycation agent and/or the composition of the invention is used before the start of the first signs of skin aging. In another embodiment, the *Garcinia kola* extract, the fraction and/or the composition of the invention is used after the appearance of the first signs of skin aging.

In one embodiment, the anti-glycation agent and/or the composition is administered once to twice per day. In one embodiment, the *Garcinia kola* extract, the fraction and/or the composition of the invention is administered in the morning and/or in the evening. Advantageously, the composition of the invention is applied to the skin by regular massage.

The invention also relates to a cosmetic treatment method, more specifically a method for preventing and/or limiting cutaneous aging in which a cosmetic composition of the invention is applied to the skin of a subject in order to fight cutaneous aging.

Method for Determining the Collagen Glycation Inhibiting Activity of a Substance The invention also relates to a method for determining the protein glycation inhibiting activity of a substance. In one embodiment, the method of the invention allows to determine the potential of a substance for inhibiting the glycation of skin proteins, preferably collagen. In a potent anti-AGEs active agent research approach, the development of this screening test was necessary: the anti-AGEs activities of substances resulting from a screening test using another protein, for example albumin, do not anticipate the inhibition capacities of the same substances on the formation of AGEs on a different protein. Indeed, as albumin has a different chemical structure from skin proteins such as collagen, the AGEs formed with these two proteins are different, and, consequently, the molecules inhibiting their formation are also different.

In one embodiment, the substance tested by the method of the invention is a compound, a mixture of compounds or an extract, preferably a plant extract.

According to an embodiment, the method of the invention comprises the following steps:
the incubation of a protein, preferably collagen, in the presence of a sugar and the substance to be tested,
the measurement of the fluorescence emitted by the glycation products formed, preferably the measurement of the fluorescence of a marker such as pentosidine.

In one embodiment, the protein is collagen, preferably type-I collagen. Type-I collagen constitutes around 90% of the collagen of vertebrates and is present in particular in the skin, in particular in the dermis. In a preferred embodiment, the target protein is calf skin collagen.

According to one embodiment, ribose is used as a sugar in the method of the invention. The use of ribose, more reactive, enables faster formation of AGEs and more specifically of pentosidine (Grandhee et al., *J. Biol. Chem.* 1991, 266, 11649-11653).

The method of the invention is suitable for identifying active agents preventing the glycation of skin proteins. The Applicant demonstrated that the method for identifying anti-glycation activities of the invention, i.e. on type-I collagen soluble in an aqueous medium, is far superior to the methods of the prior art. Indeed, the type-I collagen protein is a better model than albumin for determining the anti-glycation activities of cutaneous proteins of a compound. Moreover, the choice of a type-I collagen soluble in an aqueous medium enabled the Applicant to reduce the incubation time. Furthermore, the choice of sugar, i.e. ribose, allowed to have a much faster method than the methods of the prior art on collagen. Finally, this method is automatable and enables rapid or high-speed screening.

In one embodiment, the protein is solubilized in an aqueous solvent, preferably an aqueous acid solvent, and more preferably acetic acid. In one embodiment, the acid solvent has a concentration ranging from 0.1 to 1N, preferably 0.1N.

In one embodiment, the protein solution used to perform the test preferably has a concentration of 0.1%. In a preferred embodiment, the protein solution is a 0.1% calf skin type-I collagen solution in acetic acid 0.1N.

In one embodiment, the sugar is selected from the group comprising ribose, glucose, fructose or a mixture, preferably the sugar is ribose, and, more preferably, D-ribose.

In a first embodiment, the protein, the sugar and the substance to be tested are placed in a buffered aqueous solution, preferably a solution with a pH ranging from 6 to 8.5, more preferably a pH of 7.4. In one embodiment, the buffered solution is a phosphate buffer, preferably a phosphate buffer at pH 7.4. In this embodiment, the solution is then incubated. Preferably, the incubation step lasts for a period of 24 to 72 hours, and more preferably around 24 hours.

In a second embodiment, the substance to be tested is added to a previously incubated solution comprising the protein, the sugar and the phosphate buffer, preferably previously incubated for a period of at least 1 day, and preferably at least 1 day.

In one embodiment, the incubation step is performed at a temperature ranging from 15 to 60° C., preferably at 37° C. In one embodiment, the incubation solution has a protein concentration ranging from 0.001 to 10%, preferably from 0.01 to 1%. In one embodiment, the incubation solution has a sugar concentration ranging from 0.01 M to 1 M, preferably from 0.1 to 0.5 M. In one embodiment, the incubation solution has a concentration of substance to be tested ranging from 0.01 to 10%. The incubation ranges from 6 to 168 hours, and is preferably between 20 and 30 hours, and more preferably around 24 hours.

In one embodiment, the fluorescence measurement is performed by means of a spectrofluorometer, preferably a Tecan Infinite M200 spectrofluorometer accompanied by the Tecan Magellan software.

In one embodiment, the method of the invention is automatable. In a particular embodiment, the automation is performed by adapting the method described by Derbré et al. (*Anal. Bioanal. Chem.* 2010, 398, 1747-1758). In particular, the method of the invention can be performed using 96-well plates.

In a preferred embodiment, type-I collagen, ribose and the substance to be tested are incubated in phosphate buffer at pH 7.4 at 37° C. According to this embodiment, the reading is direct without sampling of the supernatant and the pentosidine AGEs are quantified at $\lambda_{em}$=440 nm and/or 385 nm for an excitation of $\lambda_{ex}$=370 nm and 335 nm, respectively.

Advantageously, the method of the invention enables to determine the concentration of a substance allowing to inhibit 50% ($IC_{50}$) of terminal the glycation of the substrate protein, preferably collagen, by the sugar, preferably D-ribose.

DEFINITIONS

In this invention, the terms below are defined as follows:

"anti-glycation agent" concerns molecules, mixtures or extracts inhibiting or limiting the glycation of proteins, preferably skin proteins, and in particular proteins of the dermis such as collagen. Anti-glycation agents (or AGEIB) inhibit or limit the formation of glycation end products (or AGEs).

"extract" refers to a preparation obtained by concentrating a solution resulting from the depletion of a plant or animal substance by a solvent.

"dry extract" refers to an extract of which more than 90% of the solvent has been eliminated, preferably more than 95%, or an extract that contains less than 10%, preferably, less than 5% residual solvent.

"extraction yield" refers to the ratio between the mass of matter obtained by extraction and the initial mass of the matter extracted.

"dry matter" refers to what remains of a product when the water has been removed from it. In this invention, the dry matter more specifically refers to a plant matter having been dried and comprising less than 10% water, preferably less than 6%.

"fraction" results from the fractionation of an extract, i.e. the separation of a portion of an extract.

"dry fraction" refers to a fraction of which more than 90% of the solvent has been eliminated, preferably more than 95%, even more preferably more than 98%, or a fraction containing less than 10%, preferably less than 5%, and even more preferably less than 2% solvent.

"supercritical extraction" refers to the action of extracting a substance from a mixture of substances by placing said mixture in contact with a supercritical fluid in a pressurized container so as to selectively dissolve the substance to be extracted in the supercritical fluid. The supercritical fluid filled with the substance of interest is then transferred to a separator in which it is brought to a gaseous form, thereby enabling the substance of interest to be isolated.

"supercritical $CO_2$" refers to $CO_2$, optionally mixed with a co-solvent, at temperatures above 30.95° C. and pressures above 73.8 bars.

"subcritical $H_2O$" refers to water under temperature and pressure conditions so that:
the temperature is below the critical temperature of water ($T_{critical}$=101° C.) and the pressure is above the critical pressure of water ($P_{critical}$=221 bars); or
the temperature is above the critical temperature of water ($T_{critical}$=101° C.) and the pressure is below the critical pressure of water ($P_{critical}$=221 bars).

"cosmetically acceptable" refers to a component that can be used in contact with the skin without any adverse effect such as toxicity, irritation or allergic response.

"carrier" refers to a substance with which the component of interest is mixed or dissolved. According to one embodiment, the carrier is cosmetically acceptable.

"cosmetic base" refers to a cosmetically acceptable carrier comprising a lipophilic compound.

"around" placed in front of a number, means more or less 10% of the nominal value of said number.

"kolaviron" refers to a mixture of biflavonoids obtained by polar extraction (alcohol or acetone, for example) of Garcinia kola seeds, previously degreased. This mixture is constituted primarily of 3 biflavonoids: GB1, GB2 and kolaflavanone.

"Trolox equivalent" or "TE" is the concentration of Trolox (i.e. 6-hydroxy-2,5,7,8-tetramethylchroman-2-carboxylic acid) having the same activity as the substance to be tested at a given concentration. The result is expressed in µmol of Trolox equivalent per gram of product.

"cosmetic composition" is a composition intended to be placed in contact with various surface parts of the human body, in particular the epidermis, the hair and capillary systems, the nails, the lips and the external genitalia, or with the teeth and oral mucous membranes, in order, exclusively or primarily, to clean them, apply fragrance to them, modify the appearance of them, protect them, keep them in good condition or correct body odors.

In this invention, the percentages (%) are percentages in weight relative to the total weight of the extract, the material or the main composition concerned.

EXAMPLES

This invention will be easier to understand in view of the following examples, which illustrate the invention in a non-limiting manner.

Example 1

Preparation of a Garcinia kola Extract According to the Invention

Material and Methods

Two batches of Garcinia kola were tested: one from Togo and the other of unknown origin. The two batches have the same HPLC-UV-MS profile.

Extraction

Extractions on a Büchi Speed Extractor were performed using, as the solvent: water, ethanol and a water/ethanol (50/50) mixture under the following conditions:
extraction cells: 120 mL (volume completed with sand 0.3-0.9 mm, Büchi)
temperature: 100° C.
pressure: 100 bar
collection vial: 240 mL
rinsing with solvent: 1 min
rinsing with gas: 1 min The pressurized extraction cycles are performed according to the table below:

| cycle | heating | maintenance | extraction cell drainage |
|---|---|---|---|
| 1 | 5 min | 0 | 2 min |
| 2 | 1 min | 10 min | 2 min |
| 3 | 1 min | 10 min | 2 min |

The extracts were then evaporated with the rotary evaporator (50° C.), after filtration on cotton, to obtain the different dry extracts.

A kolaviron extraction (GB1, GB1a, GB2 and kolaflavanone) was also performed according to the protocol described by Farombi et al. *Int. J. Env. Res. Public Health*, 2011, 8, 2533-2555, and slightly modified:

extraction by cyclohexane (degreasing)

extraction of the residue by acetone evaporation of the extract obtained with acetone and liquid/liquid partition of said extract between water and ethyl acetate the extract obtained corresponds to kolaviron (HPLC, TLC profile): extract enriched with biflavonoids GB1, GB1a, GB2 and kolaflavanone.

The yields of the extractions are listed below:

| Extraction solvent | Extraction yield |
|---|---|
| $H_2O$ | 10.40% |
| EtOH | 13.00% |
| $H_2O$/EtOH (50/50) | 12.90% |

Figure 1:
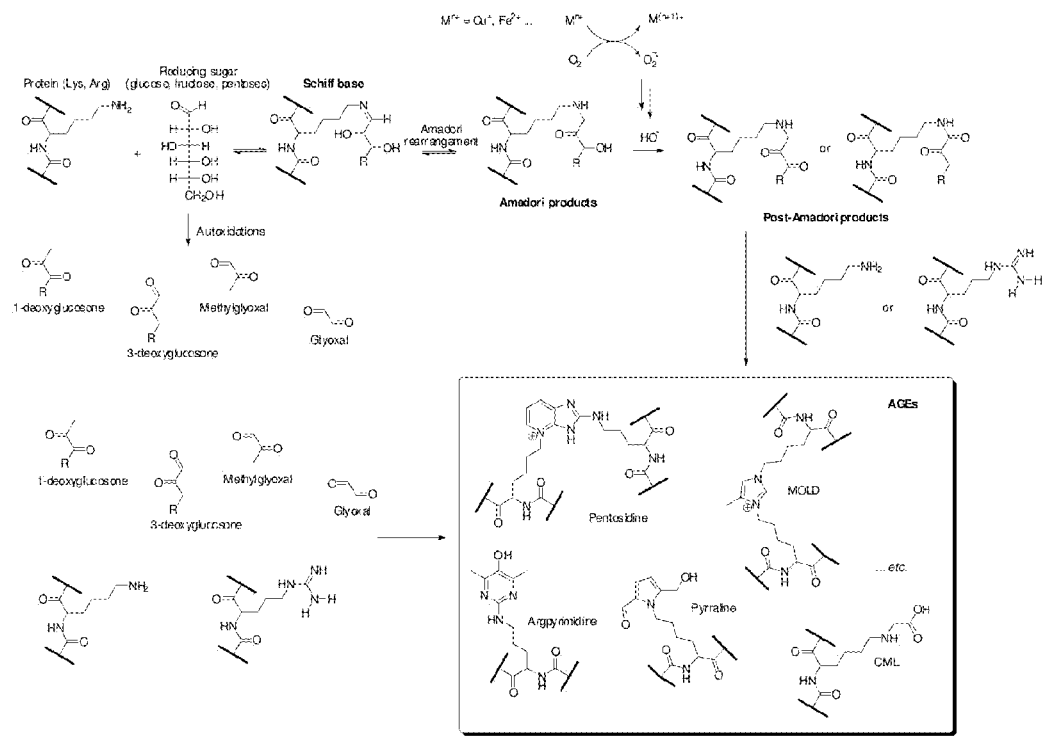
FIG. 1 is a schematic representation of the cascade of reactions leading to the formation of glycation end products.
Figure 2:
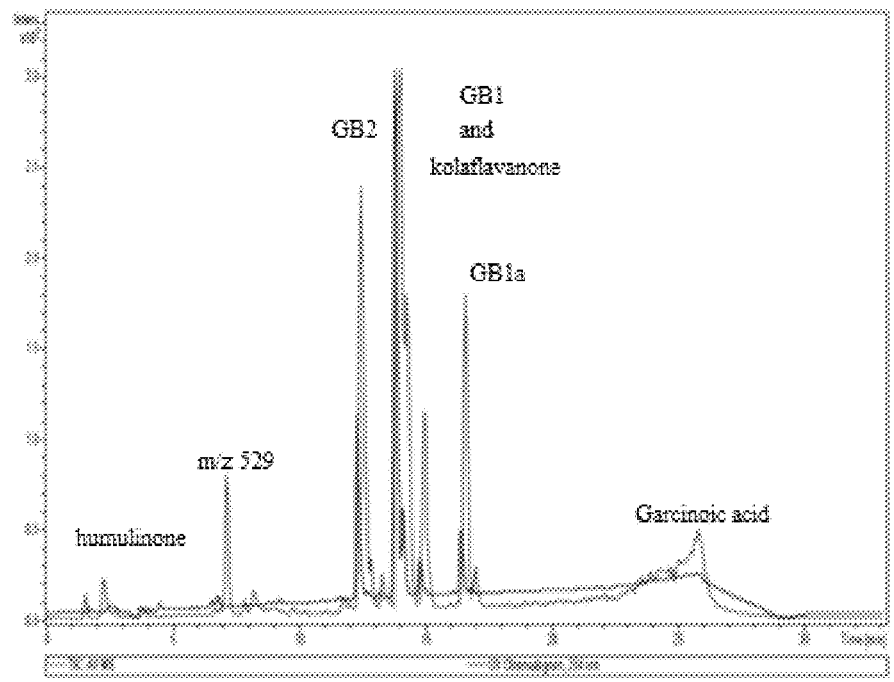
FIG. 2 is a HPLC-UV-MS profile of the ethanol extract of Garcinia kola seeds according to the invention.

HPLC Analysis of the Extracts (See FIG. 2).

The HPLC conditions used are:

Waters 2695® separation module

Photodiode Array Detector Waters® 2996 detector software: Empower® samples: 5 mg/mL in a mixture of $H_2O$/MeOH (50/50), injection of 20 μL

LiChrospher column 100 RP18 (150×4.6 mm, 5 μm, Agilent Technologies), gradient: table below (flow rate: 1 mL/min)

| time | Solvent A ($H_2O$, HCOOH 0.1%) | Solvent B (acetonitrile) |
|---|---|---|
| 0 min | 80% | 20% |
| 20 min | 35% | 65% |
| 23 min | 10% | 90% |
| 25 min | 80% | 20% |
| 33 min | 80% | 20% |

Measurement of Equivalents in GB2 of the Extracts

Calibration Curve:

20 μL of methanol solutions of GB2 at concentrations of 0.125 mg/mL, 0.25 mg/mL, 0.5 mg/mL and 1.0 mg/mL are injected in HPLC as described above. The area below the curve of the peak corresponding to GB2 (at 290 nm) is calculated for each concentration by means of the Empower software. The calibration curve representing the concentration as a function of the area of the GB2 peaks is drawn and its equation determined The equivalents in GB2 of the extracts are measured after injection in HPLC of *Garcinia kola* extract at concentrations of 0.5 and 1.0 mg/mL, as described above. The sum of the areas of the peaks corresponding to the biflavonoids in the extract is calculated by means of the Empower software. The total biflavonoid concentration in the extract is determined by means of the calibration curve.

Mass Spectrometry

The mass spectra are produced by means of an Esquire 3000 PLUS ion trap (Bruker) and are processed by the DataAnalysis software.

Example 2

Preparation of a *Garcinia kola* Extract According to the Invention 200 mg of the raw ethanol extract obtained in example 1 were fractioned on silica gel (Flash column, gradient from 100% dichloromethane to 100% MeOH), 4 fractions were obtained:

F1=garcinoic acid

F2=GB1, GB1a, GB2, kolaflavanone

F3=GB1, GB1a, GB2, kolaflavanone+polyol(s)

F4=fraction enriched with polyol(s)

Results

The absence of alkaloids in the extract was verified by using Dragendorff, Mayer and Bouchardat reagents. A TLC was also performed using the Dragendorff reagent as a developer. No spot was developed by this reagent, which confirms the absence of alkaloids in the extract.

The chromatographic profile at 254 nm essentially shows the presence of kolaviron (FIG. 2). HPLC-MS makes it possible to identify (TIC) several compounds that cannot be detected in UV: alpha acids: humulinone and an oxide derivative, as well as a tocotrienol, garcinoic acid. The peak at 7.2 min (m/z 529) could correspond to a polyol-type derivative.

Figure 3:
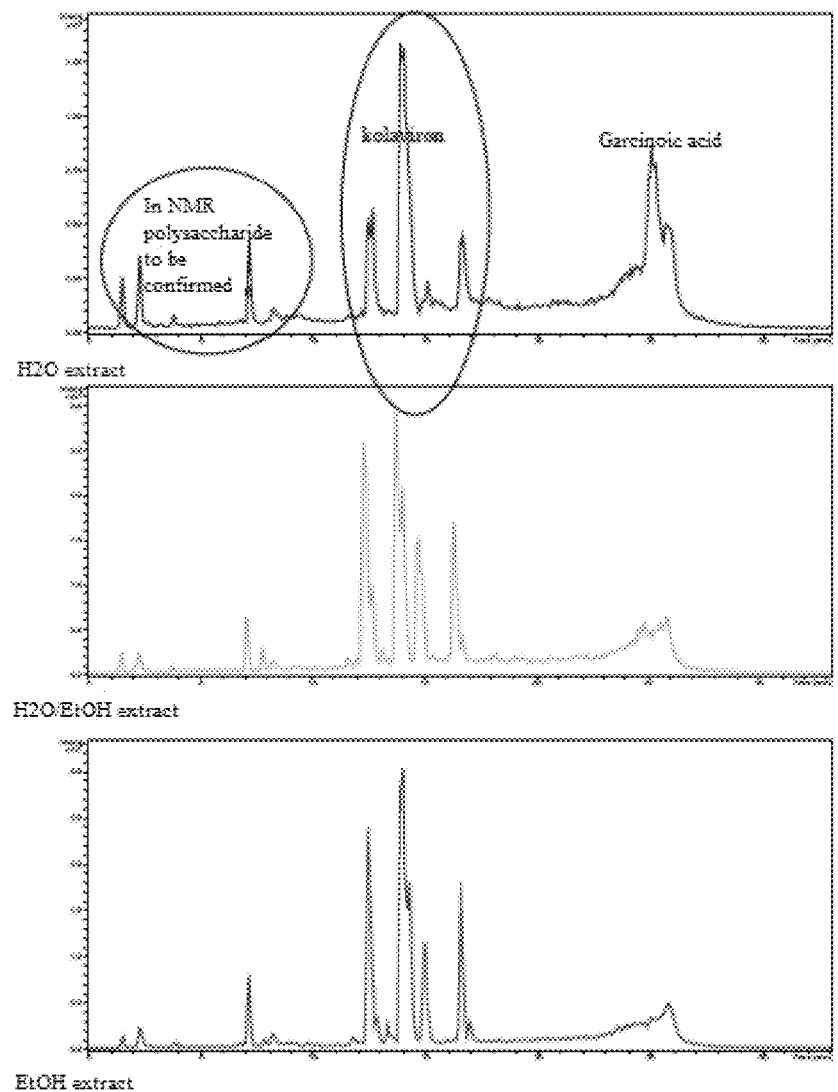
FIG. 3 shows the chromatograms of the different extracts according to the invention.

The aqueous, ethanol and hydro-ethanol extracts of *Garcinia kola* have similar chromatographic profiles (FIG. 3). It is possible, however, to note that kolaviron is present in a larger quantity in the ethanol extracts. The presence is noted in the three extracts of garcinoic acid (tocotrienol) and polar compounds the NMR of which suggests that they are polyol(s).

Example 3

Physicochemical Properties of the Ethanol Extract—Biflavonoid-Rich Extract

Total Polyphenol Assay

The quantification by HPLC-UV of the ethanol extract shows that it contains 48% biflavonoids (quantification at 290 nm expressed in equivalence of the pure biflavonoid GB2 used as an external standard). The aqueous extract contains 5% biflavonoids when the same method is used.

Physicochemical Data of the Extract

Violet-brown colored extract

Soluble in water, MeOH, EtOH, DMSO

UV spectrum: 290 nm

Melting point: 168° C. (Köpfler bank)

Example 4

Cosmetic Composition Comprising the *Garcinia kola* Extract According to the Invention: Face Cream An oil-in-water emulsion having the following composition was produced:

| INCI name | percentage (%) |
|---|---|
| AQUA | QSF |
| *ROSA DAMASCENA* FLOWER WATER | 15 |
| *SHOREA STENOPTERA* BUTTER | 2 |
| *BUTYROSPERMUM PARKII* (SHEA BUTTER) EXTRACT | 5 |
| COCO-CAPRYLATE | 1 |
| DIGLYCERIN | 5 |

-continued

| INCI name | percentage (%) |
|---|---|
| PROPANEDIOL DICAPRYLATE | 4 |
| *ROSA RUBIGINOSA* SEED OIL | 3 |
| *ZEA MAYS* (CORN) STARCH | 3 |
| CETEARYL ALCOHOL | 2 |
| GLYCERYL STEARATE | 1 |
| FRAGRANCE | 1.75 |
| OCTYLDODECYL MYRISTATE | 1.5 |
| PROPANEDIOL | 3 |
| SECALE CEREALE SEED EXTRACT | 1.5 |
| GLUCONOLACTONE | 1.1 |
| GLYCERYL UNDECYLENATE | 2 |
| POLYLACTIC ACID | 2 |
| TREHALOSE | 4 |
| CAPRYLIC/CAPRIC TRIGLYCERIDE | 3 |
| GLYCERIN | 1 |
| LAUROYL LYSINE | 2 |
| SODIUM BENZOATE | 0.5 |
| TOCOPHEROL | 0.3 |
| BENZYL ALCOHOL | 0.23 |
| XANTHAN GUM | 1 |
| SODIUM HYDROXIDE | 0.16 |
| *CHONDRUS CRISPUS* EXTRACT | 0.15 |
| *ALOE BARBADENSIS* LEAF JUICE POWDER | 0.1 |
| SODIUM HYALURONATE | 0.05 |
| DEHYDROACETIC ACID | 0.0264 |
| PHYTIC ACID | 0.025 |
| *GARCINIA KOLA* EXTRACT | 0.1-2 |

Example 5

Identification of the Formation of AGEs and Determination of an Anti-AGE Activity on Type-I Collagen Anti-AGE Activity on Calf Skin Collagen in Solution in the Presence of Ribose—Method According to the Invention Calf skin collagen (0.1 mg/mL) and ribose (0.5 M) are incubated in phosphate buffer 50 mM pH 7.4 at 37° C. in a 96-well Greiner bio-one plate with a black bottom (100 µL). The same experiment is performed in the presence of an AGE formation inhibitor, such as aminoguanidine (1 mg/mL, DMSO 10%). The following control solutions are also prepared: collagen (0.1 mg/mL) with or without an AGE formation inhibitor (1 mg/mL, DMSO 10%) is incubated in phosphate buffer 50 mM pH 7.4 at 37° C. After the incubation period, the fluorescence of the pentosidine-type AGEs ($\lambda_{exc}$ 335 nm and $\lambda_{em}$ 385 nm) is measured on an Infinite M200 apparatus (Tecan) controlled with the Magellan software (Tecan).

Example 6

Automation and Statistical Reliability of the Method of the Invention on Solubilized Collagen The method for measuring the anti-AGEs activity on calf skin collagen in solution described in example 5 was automated according to the method described by Derbré et al. in *Anal. Bioanal. Chem.* 2010, 398, 1747-1758.

The quality of the test, and therefore the possibility of performing a high-speed screening without replication, was evaluated by the calculation of the factor Z', as described by Zhang et al. (Zhang et al., J. Biomol. Screen. 1999, 4, 67-73).

Thus, in order to evaluate the quality of the screening test using calf skin collagen (0.1 mg/mL) and ribose 0.5 M, statistical parameters were calculated, comprising that of the signal-to-noise ratio (S/N), the signal-to-background noise ratio (S/B), the separation band and the statistical factor Z' according to the following calculation formulas:

$$S/N = (\mu_{c+} - \mu_{c-})/(\sigma_{c+}^2 + \sigma_{c-}^2)^{1/2}$$

$$S/B = \mu_{c+}/\mu_{c-}$$

$$\text{Separation band} = |\mu_{c+} - \mu_{c-}| - (3 \times \sigma_{c+} + 3 \times \sigma_{c-})$$

$$Z' = 1 - (3 \times \sigma_{c+} + 3 \times \sigma_{c-})/|\mu_{c+} - \mu_{c-}|$$

where $\sigma_{c+}$, $\mu_{c+}$, $\sigma_{c-}$, $\mu_{c-}$ represent the standard deviations ($\sigma$) and the means ($\mu$) of the maximum (c+) and minimum (c−) signals.

The results are as follows:

| | Mean ± S.D. |
|---|---|
| factor Z' | 0.61 ± 0.06 |
| S/N | 10.47 ± 1.53 |
| S/B | 1.60 ± 0.03 |
| Maximum signal | 303 ± 8 |
| Separation band | 69 ± 7 |
| Plate-to-plate variability (%) | 2.6 |
| Variability from one day to another (%) | 0.5 |

The results obtained show that the signal-to-background noise ratio S/B is not very high. Because of the weak dispersion of results, the signal-to-noise ratio (S/N) as well as the factor Z' are very satisfactory. The factor Z' is greater than 0.5, which enables replication to be avoided.

The results of the method of the invention therefore enable high-speed screening at a single concentration since Z'>0.5.

Example 7

Figure 4:
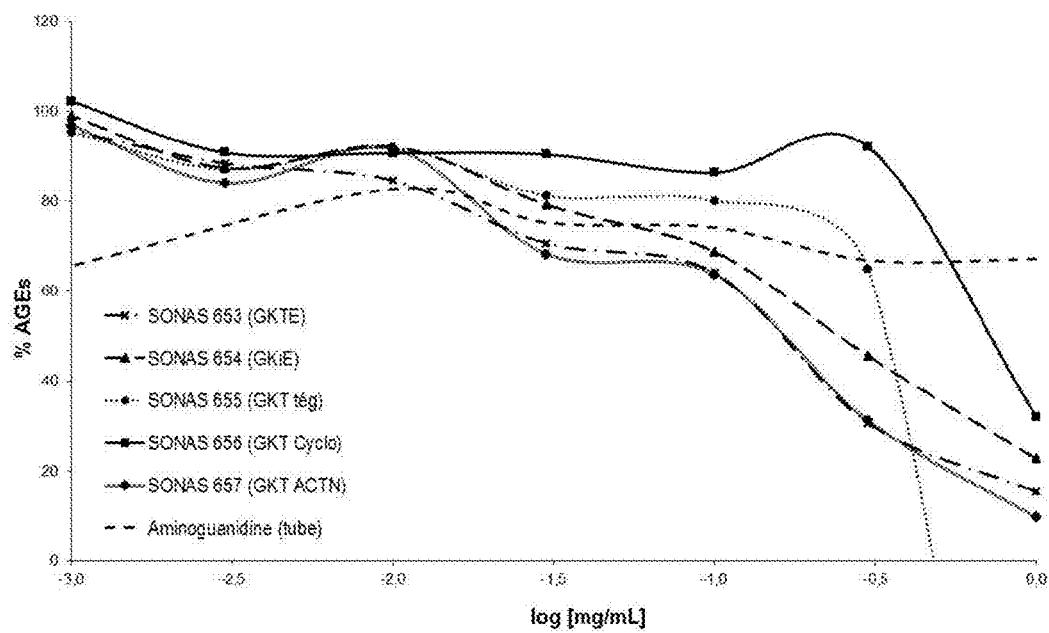
FIG. 4 is a graph showing the anti-AGEs activity of the extracts according to the invention.
Figure 4:
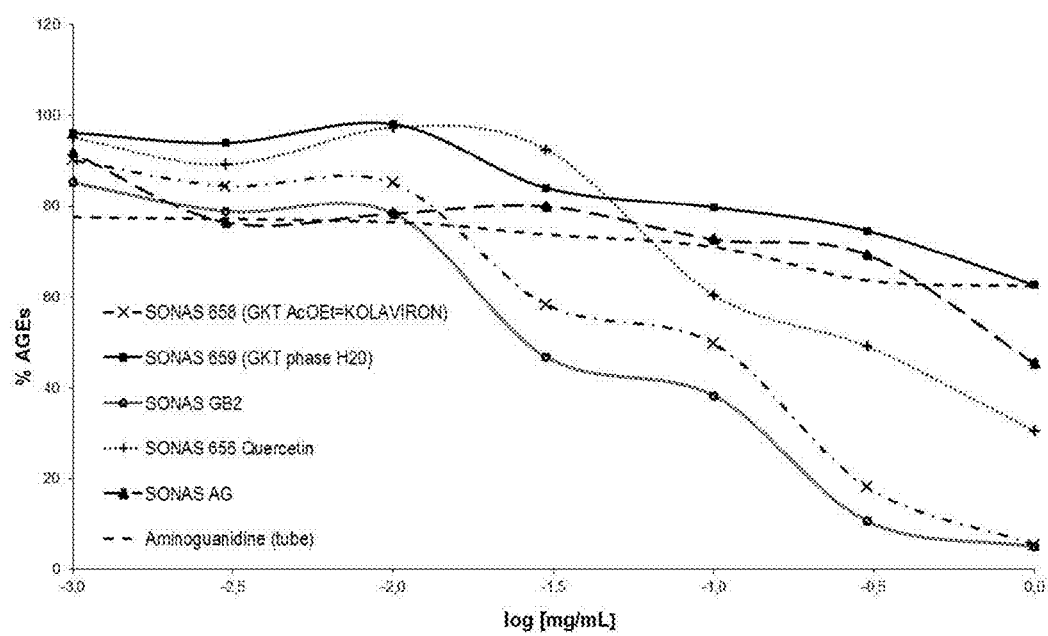
Figure 5:
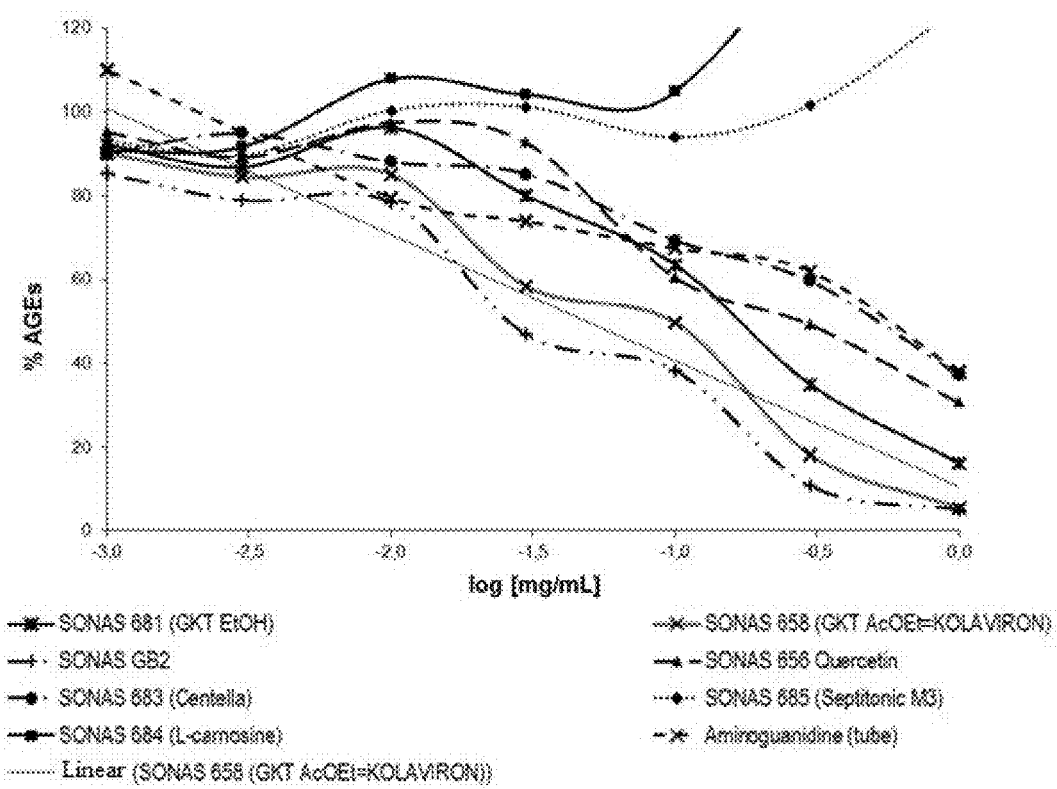
FIG. 5 is a graph showing the collagen anti-glycation activity of the ethanol extract of Garcinia kola according to the invention compared with cosmetic active agents and pure molecules.

Determination of the Anti-AGEs Activity of the *Garcinia kola* Extract According to the Invention Calf Skin Collagen The aqueous extracts as well as the intermediate extracts obtained in the kolaviron extraction were tested on collagen (FIG. 4). The aqueous extracts (GKTE and GkiE, respectively, batches from Togo and of unknown origin) have a good anti-glycation activity with an $IC_{50}$=0.16 mg/mL, an activity similar to that of kolaviron ($IC_{50}$=0.10 mg/mL). The GB2 biflavonoid shows an even better anti-AGEs activity ($IC_{50}$=0.03 mg/mL). An extraction performed on seed teguments shows that the teguments (GKT teg) do not have an anti-glycation activity.

The ethanol extract was evaluated for its anti-glycation activity on albumin, calf skin collagen and for its antioxidant potential (cf. table below). The ethanol extract has an activity substantially similar to that of kolaviron (respectively $IC_{50}$ of 0.16 and 0.10 mg/mL). The polyols present in the *Garcinia kola* extract do not have an anti-glycation activity on calf skin collagen while garcinoic acid has a real anti-glycation activity, but nevertheless inferior to that of kolaviron. This extract also has a high antioxidant potential on the two models used (DPPH and ORAC); it is also more active than the aqueous *Garcinia kola* extract on these same models.

Table of the antioxidant potential and the anti-glycation activity of the ethanol *Garcinia kola* extract and its constituents:

| | DPPH (µmol TE/g) | ORAC (µmol TE/g) | Anti-AGE activity measured on albumin* ($IC_{50}$ in mg/mL) | Anti-AGE activity measured on collagen* ($IC_{50}$ in mg/mL) |
|---|---|---|---|---|
| Ethanol extract of the invention: GKT EtOH | 693 ± 32 | 8207 ± 383 | 0.25 | 0.15 |
| Aqueous extract of the invention: GKT $H_2O$ | 255 ± 22 | 2344 ± 122 | 0.15 | 0.15 |
| AcOEt extract of GKT: Kolaviron | 1035 ± 7 | 18053 ± 89 | 0.05 | 0.1 |
| Aqueous extract of balm | 1377 ± 194 | 7618 ± 152 | 0.8 | NA |
| Ethanol extract of balm | 913 ± 335 | 4527 ± 121 | 0.3 | NA |
| Aqueous extract of St. John's wort | 840 ± 106 | 3541 ± 80 | 0.3 | NA |
| Ethanol extract of St. John's wort | 1130 ± 252 | 5608 ± 71 | 0.2 | 0.6 |
| Procyanidin B2 | 3945 | 23720 | 0.1 | NA |
| Chlorogenic acid | 2966 ± 47 | 12101 | 0.1 | n.d. |
| EtOH extract of rosemary | 591 ± 20 | 2433 | 0.6 | n.d. |
| Aminoguanidine | 0 | 0 | 0.15 | 1.0 |
| Quercetin | 6722 | n.d. | 0.06 | 0.35 | with
GKT: *Garcinia kola* from Togo
TE: Trolox Equivalent
NA: Inactive
n.d.: not determined
*Evaluation of the quantity of pentosidine-type AGEs formed The data of table 1 make it possible to observe that, while certain molecules may have both an antioxidant activity and an anti-AGE activity, this situation is far from being systematic. It can only be noted that there is no direct correlation between the antioxidant activity of a compound and its anti-AGE activity. For example, aminoguanidine does not have an antioxidant activity according to the DPPH and ORAC tests, but has an anti-AGE activity on albumin and collagen.

In addition, there is also no correlation between the anti-AGE activity of a molecule with respect to albumin glycation and the anti-AGE activity of a molecule with respect to collagen glycation. For example, aqueous extracts of balm, ethanol extracts of balm and aqueous extracts of St. John's wort have a high antioxidant activity according to the DPPH and ORAC tests, and also an anti-AGE activity on albumin, but no anti-AGE activity on collagen is observed.

This is also the case for procyanidin B2.

However, the ethanol extract of St. John's wort has both an antioxidant activity according to the DPPH and ORAC tests, and an anti-AGE activity on albumin and collagen.

In conclusion, it is observed that the aqueous and ethanol extracts of the invention appear to be more active than aminoguanidine and quercetin, which are the references for the anti-AGE tests.

The invention claimed is:

1. A cosmetic treatment method for inhibiting glycation of proteins, comprising applying to the skin of a subject a cosmetic composition to inhibit glycation of proteins, wherein said cosmetic composition comprises:
   an anti-glycation agent including a *Garcinia kola* extract, said *Garcinia kola* extract comprising a total biflavonoid concentration of more than 5% biflavonoids expressed in GB2 equivalents, assayed by HPLC-UV at 290 nm, wherein at least one of said biflavonoids is selected from the group consisting of GB1, GB1a, GB2 and kolaflavanone, and wherein said *Garcinia kola* extract is 0.1 to 2% by weight of said cosmetic composition; and
   at least one compound selected from the group consisting of consistency factors, emollients, emulsifiers, surfactants, thickeners, moistening agents, gelling agents, fragrances, preservatives, dyes and pH adjusters.

2. The cosmetic treatment method according to claim 1, wherein the *Garcinia kola* extract is obtained by extraction from *Garcinia kola* seeds.

3. The cosmetic treatment method according to claim 1, wherein the *Garcinia kola* extract comprises garcinoic acid.

4. The cosmetic treatment method according to claim 1, wherein the cosmetic composition is an oil-in-water emulsion.

5. The cosmetic treatment method according to claim 1, wherein the total biflavonoid concentration of the *Garcinia kola* extract is more than 20% biflavonoids expressed in GB2 equivalents, assayed by HPLC-UV at 290 nm.

6. The cosmetic treatment method according to claim 1, wherein the total biflavonoid concentration of the *Garcinia kola* extract is more than 40% biflavonoids expressed in GB2 equivalents, assayed by HPLC-UV at 290 nm.

* * * * *